United States Patent [19]
Cecil

[11] Patent Number: 5,808,265
[45] Date of Patent: *Sep. 15, 1998

[54] QUALITY CONTROL STORAGE DEVICE

[76] Inventor: Dimitrios G. Cecil, 1277 Ashover Dr., Bloomfield Hills, Mich. 48304

[ * ] Notice: The term of this patent shall not extend beyond the expiration date of Pat. No. 5,614,109.

[21] Appl. No.: 783,560

[22] Filed: Jan. 14, 1997

Related U.S. Application Data

[63] Continuation of Ser. No. 498,776, Jul. 5, 1995, Pat. No. 5,614,109.

[51] Int. Cl.$^6$ .................................................. B23K 11/25
[52] U.S. Cl. ........................................... 219/109; 198/341
[58] Field of Search .................................... 219/109, 110; 198/341; 209/546, 548

[56] References Cited

U.S. PATENT DOCUMENTS

| | | | |
|---|---|---|---|
| 4,275,830 | 6/1981 | McDonald | 232/43.1 |
| 4,387,064 | 6/1983 | Werderitch et al. | 264/40.1 |
| 4,447,700 | 5/1984 | Cohen | 219/117.1 |
| 4,542,277 | 9/1985 | Cecil | 219/109 |
| 4,562,330 | 12/1985 | Hamilton | 219/110 |
| 4,684,778 | 8/1987 | Cecil | 219/89 |
| 4,787,143 | 11/1988 | Yagi et al. | 29/833 |
| 4,861,959 | 8/1989 | Cecil | 219/89 |
| 5,026,972 | 6/1991 | Kanehara et al. | 235/32 |
| 5,128,507 | 7/1992 | Drake | 219/110 |
| 5,186,887 | 2/1993 | Yaginuma | 376/248 |
| 5,197,186 | 3/1993 | Strong et al. | 29/863 |
| 5,220,145 | 6/1993 | Cecil et al. | 219/110 |
| 5,254,828 | 10/1993 | Stiebel | 219/110 |
| 5,288,968 | 2/1994 | Cecil | 219/89 |
| 5,376,766 | 12/1994 | Higgins | 219/61.5 |
| 5,614,109 | 3/1997 | Cecil | 219/109 |

FOREIGN PATENT DOCUMENTS 1 128 326   4/1962   Germany .

Primary Examiner—Clifford C. Shaw
Attorney, Agent, or Firm—Brooks & Kushman P.C.

[57] ABSTRACT

Control systems and methods for inspecting at least one of a plurality of parts using an inspection station are disclosed. A comparator coupled to the inspection station compares a test signal responsive to a measured parameter of a part in the inspection station to a reference signal to determine if the part matches a predetermined profile. The comparator then provides a fault signal which disables the inspection station upon determining that a part matches the predetermined profile. The profile matching part is then removed from the inspection station and stored in a storage device. The storage device then provides a confirmation signal to the comparator indicating that the profile matching part has been stored in the storage device. The comparator then enables the inspection station upon receipt of the confirmation signal. The control systems and methods of the present invention may be incorporated in a production line adapted to index at least one of the plurality of parts into and then out of the inspection station.

25 Claims, 6 Drawing Sheets

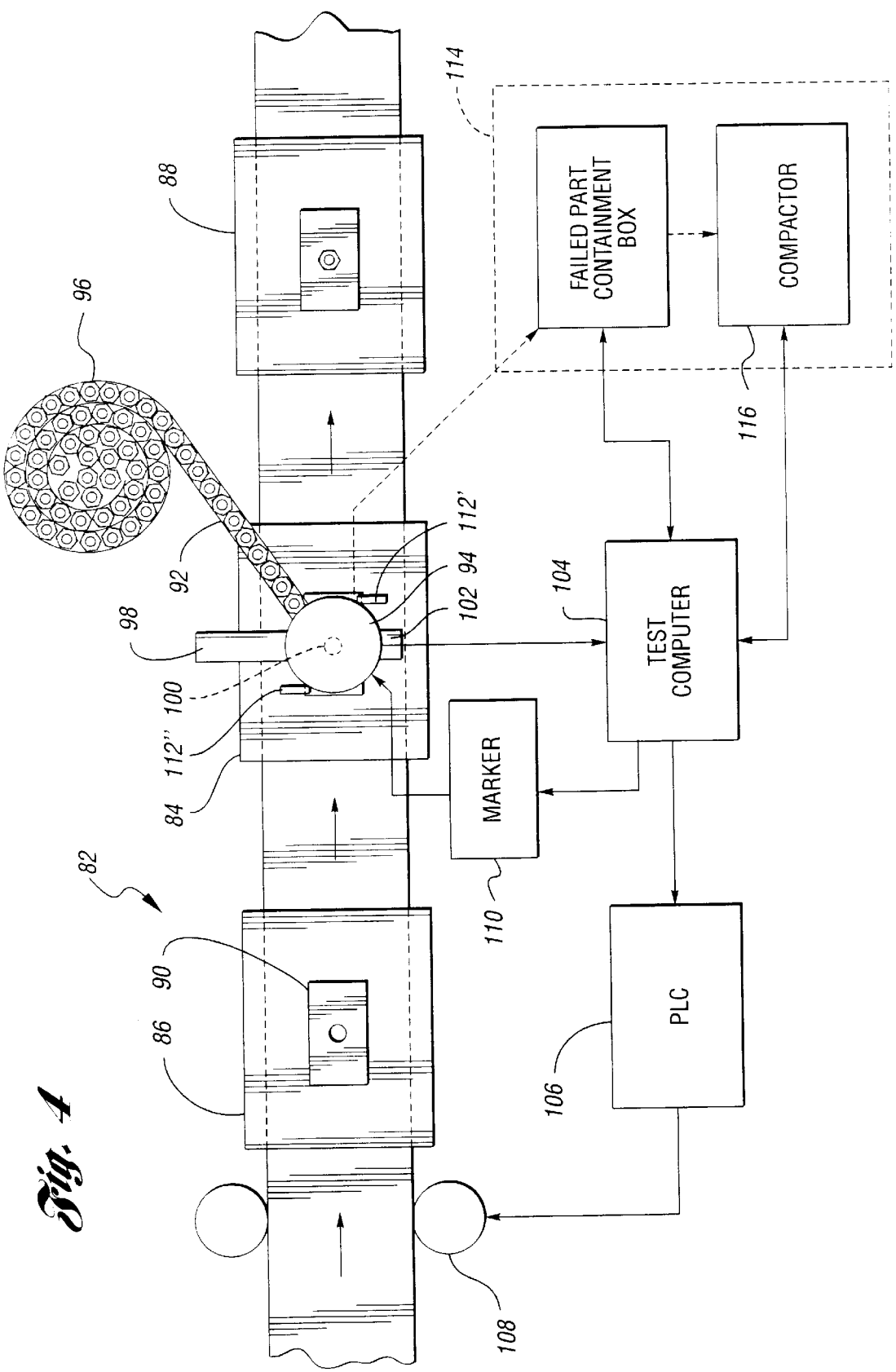

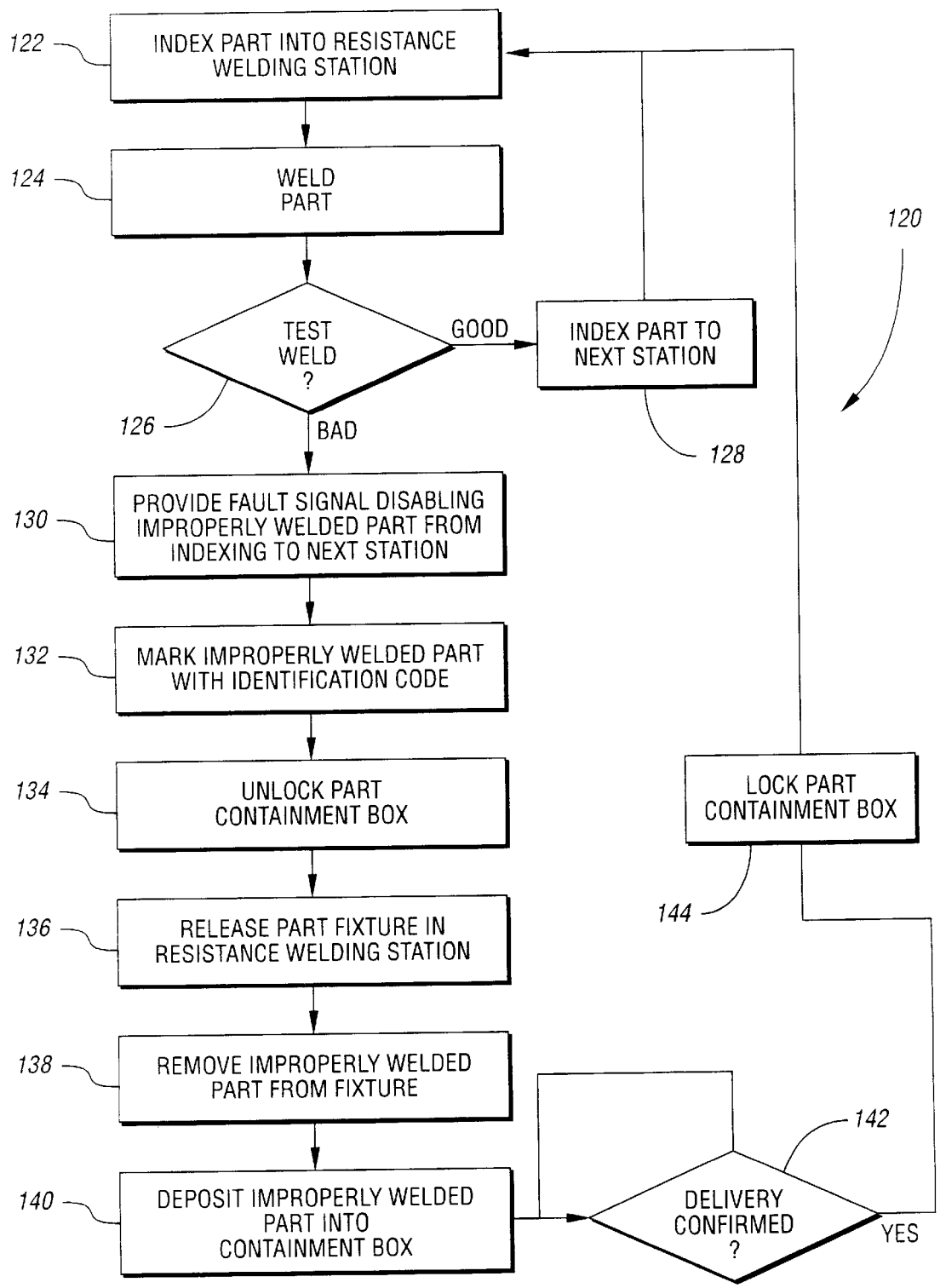

QUALITY CONTROL STORAGE DEVICE

CROSS-REFERENCE TO RELATED APPLICATION

This is a continuation of application Ser. No. 08/498,776, filed on Jul. 5, 1995, now U.S. Pat. No. 5,614,109, entitled "Welding Line With Quality Control Storage Devices", and assigned to the assignee of the present invention.

TECHNICAL FIELD

This invention relates to a system and apparatus for storing defective parts.

BACKGROUND ART

During a production line manufacturing process such as a part welding line or a part assembly line, on occasion, defective parts are manufactured. It is important to identify and remove these defective parts and ensure that they remain segregated from good parts so that they are not subsequently incorporated into a finished article sold to a consumer or used. It is advantageous to identify defective parts as soon as possible so that those parts can be removed from the production line before additional expenses associated with further machining or assembly are incurred and prior to incorporation of the defective part into a larger assembly.

There have been a number of systems generated, particularly for resistance welding, which inspect a part automatically as the part is being processed. In applications such as resistance welding, non-destructive physical testing is difficult, if not impossible, to conduct. For this reason, a number of inspection systems have been developed to identify effectively welded or formed parts automatically during and after the part forming process.

Examples of such systems are shown in U.S. Pat. No. 4,387,064 to Werderitch et al., U.S. Pat. No. 4,562,330 to Hamilton, U.S. Pat. No. 5,197,186 to Strong et al., U.S. Pat. No. 5,128,507 to Drake, U.S. Pat. No. 5,254,828 to Stiebel and a series of U.S. patents obtained by the present applicant: U.S. Pat. No. 4,542,777, No. 4,684,778, No. 5,220,145, and No. 5,288,968. The previously identified systems identify the defective parts but frequently require the operator to remove the defective part from the production line and place it in a defective part bin. U.S. Pat. No. 4,387,064 automatically places the defective parts in a defective part bin. Similarly, U.S. Pat. No. 5,186,887, which discloses a system for inspecting nuclear fuel pellets, automatically deposits defective pellets in an appropriate box.

One of the problems that the present invention solves is that machine operators frequently incorrectly assume that the automatic parts inspection operation committed an error when a part which looks perfectly good is rejected. On occasion, operators will pass the rejected part, as opposed to removing the part from the production line, which ultimately causes defective parts to be incorporated into finished goods. Inclusion of defectively welded parts into a production vehicle, for example, can result in expensive warranty repairs or product recall. On some occasions, the defectively welded part will fail during a subsequent manufacturing operation and will not even make it out of the plant. For example, weld nuts which are improperly attached to an assembly may subsequently break off during the nut tapping process or when a fastener is subsequently attached. If the product incorporating the weld nut is an advance stage of assembly, the cost and expense for repairing a defectively welded part can be significant.

Accordingly, it is an object of the present invention to provide a method and apparatus for ensuring that defective parts which are identified at an inspection station in a production line are promptly removed and placed in a defective part containment box.

It is another object of the present invention to provide a method and apparatus for marking defective parts prior to placement in the part containment box so that a manufacturer can ensure that all parts identified as being defective are properly discarded.

Yet another object of the present invention is to provide a method and apparatus which forecloses the possibility of a situation occurring where a part identified as being defective is passed on as a good part by the production operator who, with good intentions after a visual inspection, incorrectly believes that the part is not defective.

Another object of the present invention is to provide a method and apparatus for identifying parts exhibiting a predetermined characteristic at a production line inspection station which requires the identified part to be removed and securely stored prior to resuming operation of the production line.

SUMMARY OF THE INVENTION

The present invention includes a control system and method for inspecting a plurality of parts on a production line having an inspection station and a production line drive. The inspection station identifies parts which have a specific predetermined characteristic. The control system includes a test sensor coupled to the inspection station for generating a test sensor signal responsive to a characteristic of a part being measured in the inspection station. A part containment box is provided for receiving and storing the parts identified by the inspection station. The part containment box is provided with an input sensor for generating an input sensor signal when an identified part is deposited into the part containment box. A test computer is coupled to the test sensor, the input sensor of the part containment box, and the production line drive. The test computer compares the test sensor signal to the predetermined characteristic to identify the parts having the predetermined characteristic and to provide a fault signal which disables the indexing of the production line until the identified part has been removed from the inspection station and deposited into the part containment box whereupon the test computer receives the input sensor signal and thereby reenables the production line.

Further, in carrying out the above objects, the present invention includes a method for inspecting at least one of a plurality of parts using an inspection station having an associated storage device. The method includes testing a part in the inspection station to determine if the part matches a predetermined profile A fault signal which disables the inspection station is then provided upon the determination that a part matches the predetermined profile. The profile matching part is then removed from the inspection station and stored in the storage device. A confirmation signal which enables the inspection station is then provided when the profile matching part is removed from the inspection station and stored in the storage device.

Still further, in carrying out the above objects, the present invention includes a system for inspecting parts using an inspection station adapted to generate a data signal responsive to a monitored part characteristic. The system includes a storage device for storing parts. The storage device is operable to generate a confirmation signal when a part is stored therein. A comparator is coupled to the inspection station and the storage device. The comparator is operable to compare the data signal to a reference signal to determine if a part in the inspection station matches a predetermined profile. The comparator is further operable to provide a fault signal for disabling the inspection station upon determining that a part matches the predetermined profile. The comparator disables the inspection station until receipt of the confirmation signal from the storage device indicating that the profile matching part has been removed from the inspection station and stored in the storage device. The comparator then enables the inspection station.

BRIEF DESCRIPTION OF THE DRAWINGS

FIG. 4 is a schematic diagram of a resistance welding station in a production line;

FIG. 5 is a flow chart of a control system and method utilized with a resistance welding embodiment of the present invention.

BEST MODES FOR PRACTICING THE PREFERRED EMBODIMENT

Figure 1:
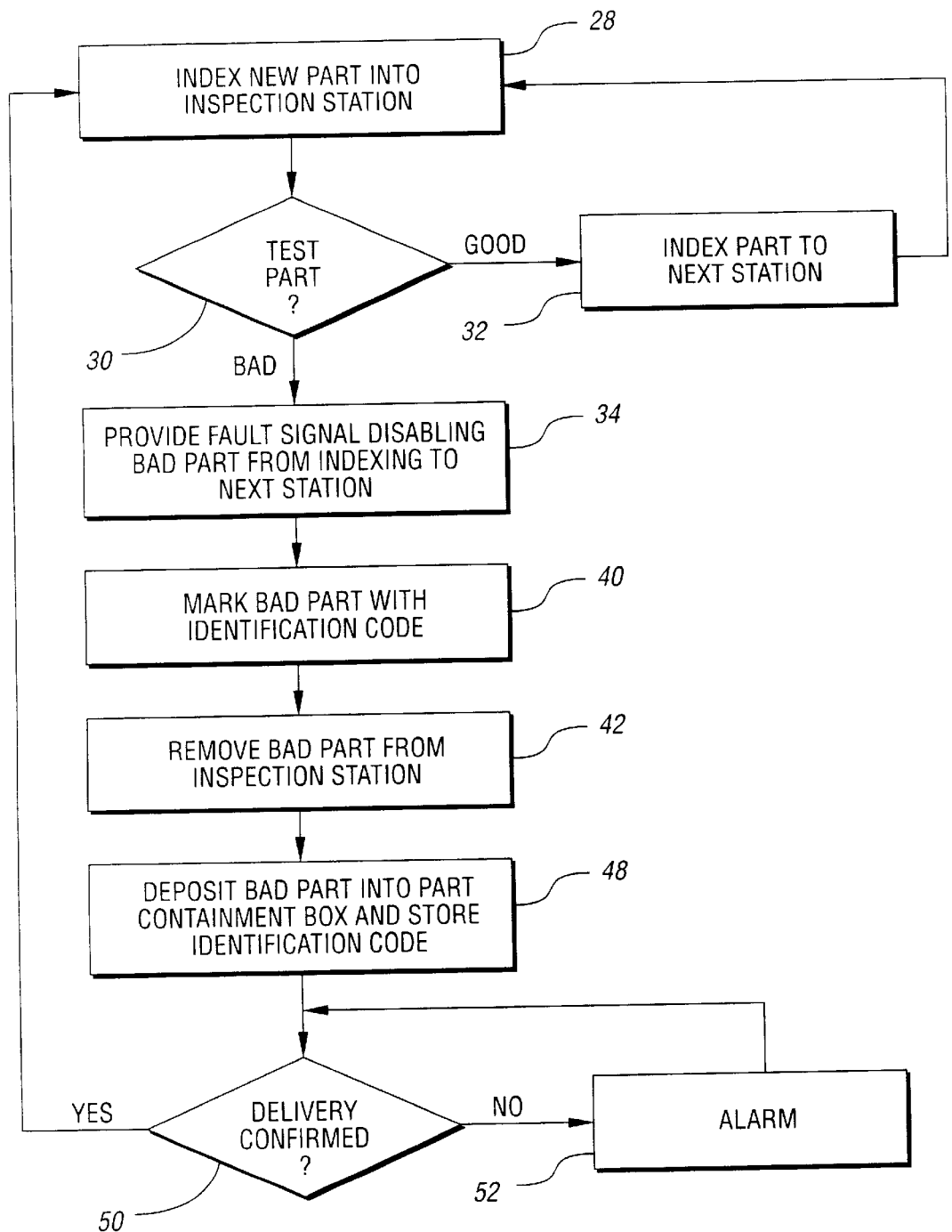
FIG. 1 is a flow chart illustrating a control system and method according to the present invention.
Figure 2:
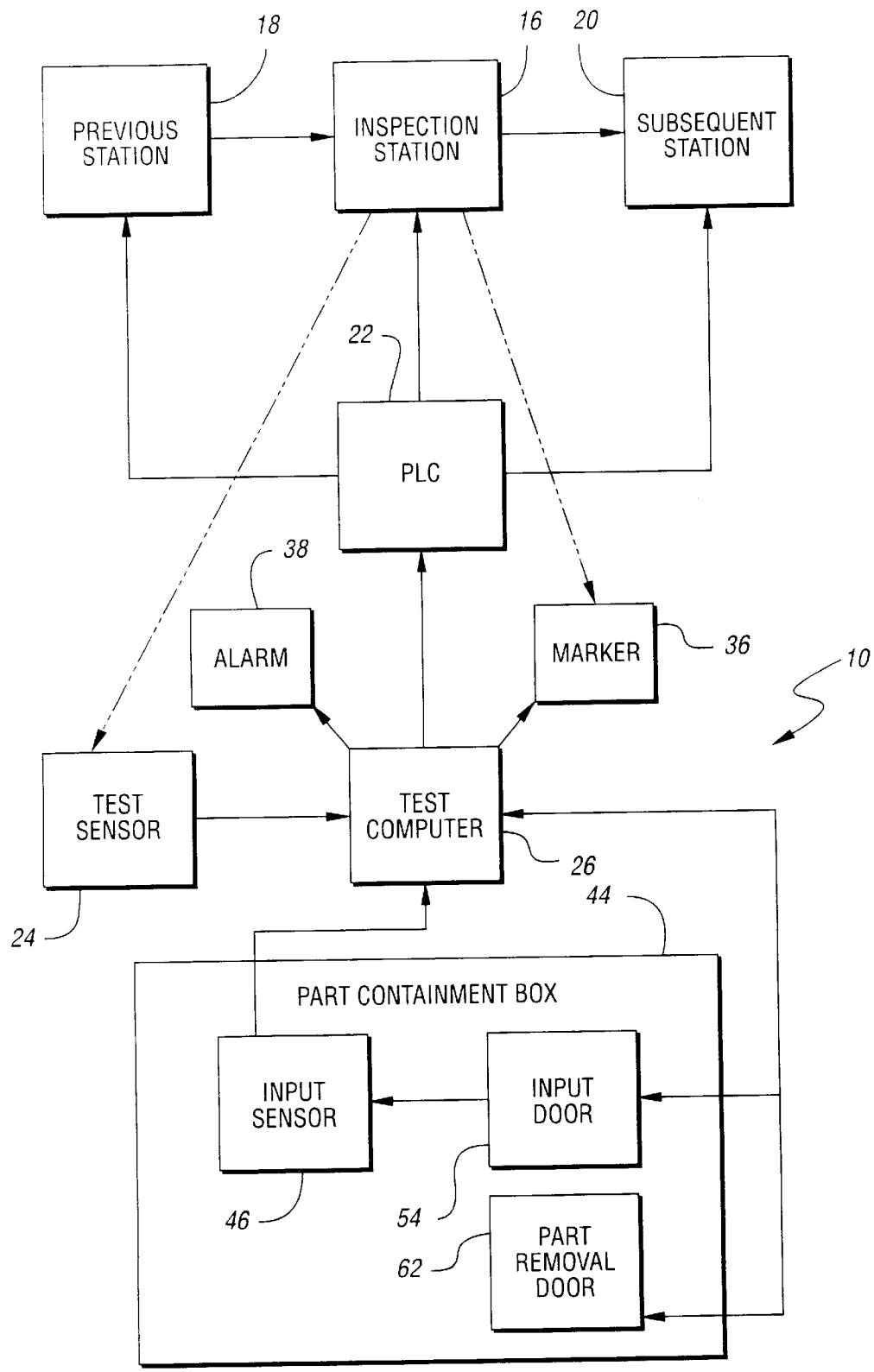
FIG. 2 is a schematic block diagram illustrating a system and method according to the present invention.

FIGS. 1 and 2 illustrate a method block diagram 10 in a control system 12 utilized for practicing the present invention. In the embodiment disclosed, the control system 12 of the present invention is utilized in conjunction with a production line 14 which includes an inspection station 16 and an immediately adjacent previous station 18 and an immediately adjacent subsequent station 20. During the normal operation of the production line 14, a programmable logic controller (PLC) 22 regulates the indexing of parts from station to station. Parts are routinely transferred from previous station 18 into inspection station 16 where the parts are inspected and, upon satisfactorily passing the inspection, are transferred to subsequent station 20. In the preferred embodiment, inspection station 16 will also provide a concurrent functional operation, such as welding or forming the part, as the inspection operation is being conducted. A test sensor 24 is provided for inspecting a measured parameter of the part in inspection station 16. Test sensor 24 provides a test sensor signal responsive to the inspected parameter. The test sensor signal is provided to test computer 26 which conducts an analysis to determine whether the measured parameter is within a predetermined range. In the preferred embodiment illustrated in FIGS. 1 and 2, if the test computer 26 indicates that the part is good, PLC 22 will cause the parts to index from station to station transferring the inspected part from station 16 to subsequent station 18 and transferring a new part from previous station 18 into inspection station 16 whereupon the process will be repeated.

With reference to the method block diagram 10 shown in FIG. 1, the first step is illustrated in block 28 which indexes a new part into the inspection station 16. The part is then tested in block 30. Good parts are indexed to the next station illustrated by block 32. If test computer 26 indicates that the part is bad, then test computer 26 will provide a fault signal disabling the part from indexing to the next station as illustrated by block 34. Test computer 26 is coupled to the PLC 22 which in turn inhibits production line movement. Optionally, a part marker 36 (illustrated in FIG. 2) is provided to appropriately identify the bad parts so that subsequently they may be monitored and evaluated. The part marker 36 can be as simple as merely marking the bad part with a dot of paint or, alternatively, the part marker 36 could apply a bar code having indicia indicating date and time, part number, and the nature of the fault detected. The test computer 26 upon sensing the occurrence of a bad part will provide a brief alarm signal to the machine operator via alarm 38 (shown in FIG. 2). Logic can be added to limit the maximum number of bad parts which can be made within a set prior to shutting down.

Still referring to the method block diagram 10 of FIG. 1, subsequent to the fault signal being provided by the test computer which disables the indexing of the defective part to the next station, as shown in block 34, the step of marking a bad part with an identification code is provided in block 40. As previously indicated, the step of marking the part is optional. In some applications, good parts will be marked or identified as explained below. Once the bad part is identified and the operator is notified either by an alarm or a work flow stoppage, the operator removes the is bad part from the inspection station 16 as illustrated in block 42. The operator then deposits the bad part into a failed part containment box 44 (shown schematically in FIG. 2) as illustrated by block 48. Once a failed part is received in failed part containment box 44, an input sensor 46 generates an input sensor signal which is transmitted to test computer 26. The test computer 26 enables the production line 14 upon receiving the input sensor signal.

In some applications, it might not be possible to immediately remove a bad part at the inspection station due to physical and plant limitations. In such applications, the test computer will keep track of the bad part and delay the step for providing a fault signal until the part is at a station in which it can be removed by an operator or robot, whereupon a delayed fault signal will be provided requiring the operator to remove the failed part and place it in the failed part containment box as previously described.

As schematically shown in FIG. 1, upon the deposit of the bad part in the failed part containment box 44, a test for confirming delivery shown in block 50 is provided within the test computer 26 in response to the input sensor signal generated by input sensor 46. If delivery of the defective part is confirmed within a predetermined time period, production resumes and the previously described sequence of the method steps takes place with a new part being indexed into the inspection station 16 as illustrated by block 28 in method block diagram 10. In the event that the delivery of the defective part to the failed part containment box 44 is not confirmed within the predetermined time period, an alarm signal is provided as illustrated by block 52.

In the preferred embodiment of the control system 12, failed part containment box 44 is provided with an input door 54 as shown in FIG. 2. Input door 54 is normally locked when the production line 14 is running. Input door 54 seals the part containment box 44 for preventing the input or the withdrawal of parts contained therein. Upon detection of a bad part, a fault signal is generated which disables the production line 14 and unlocks the input door 54. The operator then removes the defective part from the inspection station and is allowed access to place it into the failed part containment box 44 through the unlocked input door 54. Upon the input sensor 46 detecting the deposit of a failed part, the input sensor signal is transmitted to the test computer 46 which causes input door 54 to lock and the production line 14 is enabled. Failed part containment box 44 is also provided with a part removal door 62 for allowing the removal of the defective parts therein by an authorized user.

In the preferred embodiment illustrated in FIGS. 1 and 2, the control system 12 is used with a multi-station conventional production line in which defective parts are an infrequent occurrence. Thus, the defective parts are deposited in part containment box 44. This method, however, is also adaptable to sorting systems in which parts or objects are being transferred along a production line having an inspection station where the system is used to sort out good parts having a predetermined characteristic from a group of parts which are predominantly bad. In such an instance, the part containment box is provided for receiving the parts identified as good, rather than bad. The part containment box is provided with an input sensor for generating an input sensor signal when a good part is placed into the part containment box. As with the previous example, the test computer is coupled to the test sensor, the input sensor of the part containment box, and the production line. The test computer evaluates the test sensor signal to determine whether or not the part being measured in the inspection station has the predetermined characteristic. When the test computer determines that the part meets the predetermined characteristic, a signal is provided which disables the indexing of the production line until the input sensor signal is received indicating that the good part has been removed from the inspection station and deposited into the part containment box.

It should be appreciated that the method of the present invention and the associated control system, while illustrated in the drawings in association with a resistance welding production line, is useful in a variety of non-welding applications. The system is particularly useful where it is difficult to visually inspect parts, especially in instances when the problems associated with the failure to promptly detect a failed part are significant as in the case of many safety-related components of consumer products, motor vehicles, or aircraft. It should be also appreciated that the inspection operation could be utilized to inspect electronic devices such as circuit boards or the like prior to insertion into a finished product. The method and apparatus of the present invention provide a secure and safe way of handling parts identified as defective or acceptable, depending on the application, to ensure that they are not inadvertently passed on to a customer.

It should also be appreciated that the control method and apparatus according to the present invention could be realized in the form of hardware, software, or a combination thereof. Furthermore, the functions of test computer 26 could be integrated into PLC 22 if desired. Likewise, test computer 26 could be utilized to control inspection station 16.

Figure 3A:
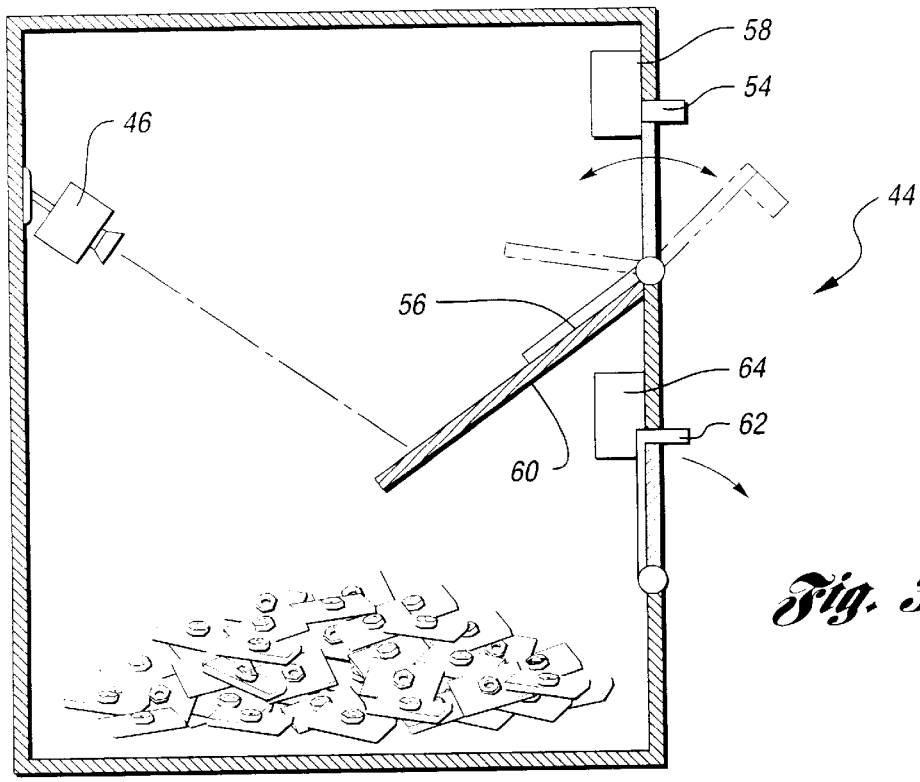
FIG. 3a illustrates a part containment box according to the present invention.

FIG. 3a illustrates part containment box 44 in cut-away side elevation. It should be appreciated that part containment boxes can be made of a variety of shapes and sizes dictated in large part by the size of the parts to be stored therein. In the illustrative part containment box 44 shown in FIG. 3a, the box is of similar size and configuration to a U.S. Mail Deposit box. Input door 54 is pivotally attached to box 44 and shifted between a closed position illustrated and an opened position shown in phantom outline. Preferably, input door 54 is provided with an inner member 56, rigidly attached to input door 54 at an angle a, similar to a U.S. Mail box door, which partially obscures the door opening to prevent the removal of parts from within the interior of part containment box 44. A remotely controlled lock assembly 58 is provided inside part containment box 44 for locking input door 54 in the closed position during normal operation. Sensor 46 is located in the interior of the part containment box 44 and is positioned to sense the deposit of a part into the part containment box 44. Sensor 46 is preferably an optical sensor, but could also be a non-contact proximity switch, sensor, or the like. The part containment box 44 is sized according to the parts to be stored and could be as large as a room size enclosure capable of storing entire car bodies.

The failed part containment box 44 is provided with an internal slide baffle 60 which is downwardly inclined and mounted adjacent to input door 54. Parts deposited in the box slide down slide baffle 60 and are sensed by input sensor 46 before falling into the bottom of box 44. Part removal door 62 is located in the lower region of box 44 to facilitate part removal. Part removal door 62 is locked by a lock sensor combination 64. Lock sensor 64 cooperates with the test computer 26. In order for an operator to remove parts from the failed part containment box 44, an appropriate authorized user code must be entered in the test computer 26. Test computer 26 then causes lock sensor 64 to release part removal door 62. Test computer 26 will make an appropriate recording of time and date and authorized user code whenever part containment box 44 is accessed either through part removal door 62 or input door 54. Preferably, lock sensor 64 will also provide a door open signal to test computer 26 requiring part removal door 62 to be securely locked prior to the resumption of the indexing of the parts and to provide a tamper signal in the event that the part removal door 62 is forced open without entry of the authorized user code. Lock sensor 64 and lock assembly 58 are preferably of similar construction, both capable of locking the respective doors closed securely in response to test computer 26 while also providing an input signal to test computer 26 indicative of door opened or closed status.

Figure 3B:
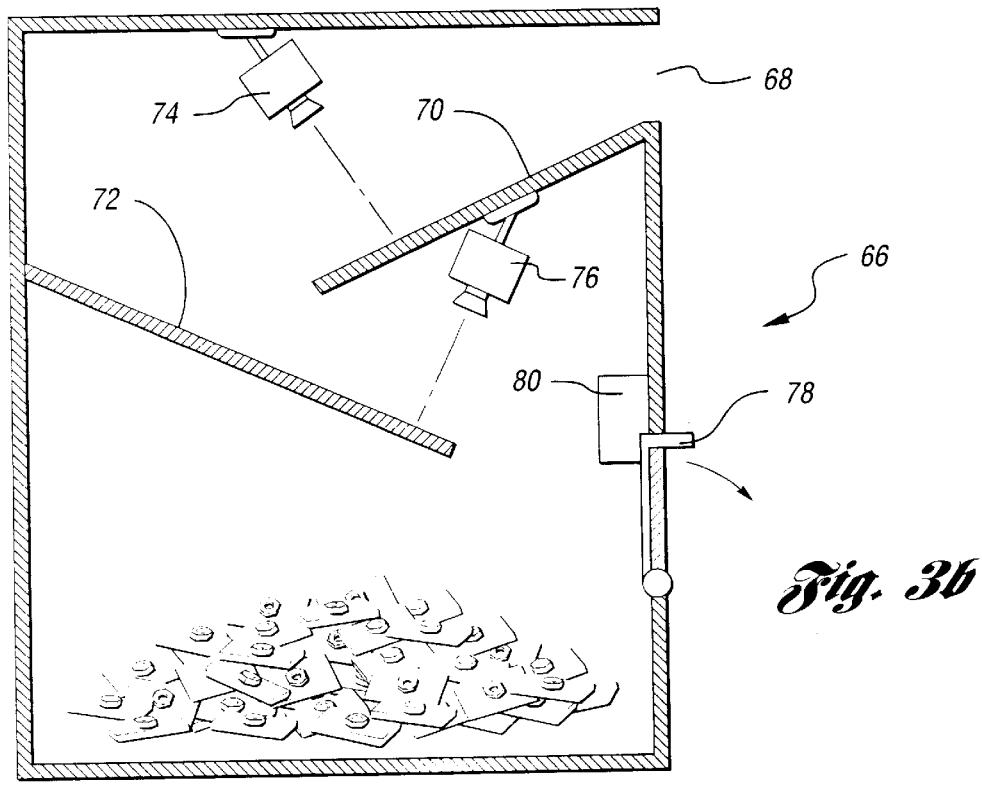
FIG. 3b is an alternative embodiment of a part containment box according to the present invention.

FIG. 3b illustrates an alternative part containment box embodiment 66. Part containment box 66 is provided with an open inlet chute 68 for insertion of marked parts. Inlet chute 68 is preferably sized to receive the desired parts while limiting the deposit of larger or differently shaped parts. Part containment box 66 is further provided with a pair of slide baffles 70 and 72 along which incoming parts will cascade. Located adjacent each slide baffle 70 and 72 is a part sensor 74 and 76 to detect the insertion of a failed part. Since inlet chute 68 is open, the pair of part sensors 74 and 76 are provided at spaced apart locations to ensure that a failed part has actually been deposited in box 66 as opposed to the sensors being activated by an operator's hand or a part which is deposited and subsequently withdrawn by the operator, a robot, or an automated unload mechanism. Part containment box 66 is also provided with an outlet door 78 having a combination door/lock sensor 80 functioning in the manner described with reference to part removal door 62 and lock sensor 64 in the FIG. 3a embodiment.

FIG. 4 illustrates a resistance welding production line 82 having a resistance welding station 84, a previous station 86, and a subsequent station 88. A part 90 is transferred into the welding station 84 where a weld nut 92 will be welded to the part 90 by weld gun 94. Weld nut 92 is fed into the welding station 84 by a pole feeder 96 and is placed onto the part 90 to be welded by an appropriate pick and place device 98. The weld gun 94 is provided with a displaceable conventional welding electrode 100 which is displaceable relative to the part 90 as weld nut 92 is welded thereto. Displacement sensor 102 is coupled to the welding electrode 100 and generates a displacement sensor signal responsive to the displacement of the welding electrode 100 relative to the parts being welded together. The displacement sensor signal is provided to test computer 104 which compares the displacement sensor signal to a predetermined desired displacement profile.

The evaluation of the displacement sensor signal can be conducted post-weld or during the welding process in real-time as described in more detail in the prior patents of Applicant cited in the Background Art section. As described previously, test computer 104 communicates with a PLC 106 which controls the operation of a production line drive 108. Test computer 104 also cooperates with a part marker 110 in order to mark defective parts. In the event the welding station 84 is provided with weld fixture clamps 112' and 112", the test computer 26 will cooperate with the clamps 112' and 112" in order to release the part 90 to enable the system operator to remove the identified part prior to deposit in a part containment box 114.

As illustrated in FIG. 4, part containment box 114 may be provided with a compactor 116. Compactor 116 may be part of the box or an adjacent component. In situations where the failed parts are not repairable, it may be advantageous to install a compactor or shredder within part containment box 114 to ensure that failed parts are destroyed and can never subsequently be sold or used. In situations where failed parts can, in some instances, be repaired or salvaged, compactor 116 may be an adjacent accessory which is used to destroy parts determined to be unrepairable after inspection. Compactor 116, whether part of part containment box 114 or a separate component, is preferably coupled to test computer 104 so that data regarding the ultimate disposition of the parts can be recorded.

FIG. 5 illustrates a method block diagram 120 associated with the resistance welding production line 82 of FIG. 4. Method block diagram 120 is similar to a more detailed version of method block diagram 10 shown in FIG. 1. Method block 120 begins with the step of indexing new parts into a resistance weld station, as shown in block 122. The parts are welded together in block 124 and as they are being welded, the weld is tested and a post-weld or real-time good or bad weld determination is made in block 126. In the event a good weld is made, the good part is indexed to the next station as shown in block 128. If a bad weld is made, the test computer provides a fault signal disabling the improperly welded part from indexing to the next station as shown in block 130. Preferably, the test computer will signal a part marker to mark improperly welded parts with an identification code as shown in block 132. If a locked part containment box is utilized, the test computer will provide a signal unlocking the failed part containment box as shown in block 134 and if the part is retained in the welding station by fixture and/or the welding electrode, the test computer will cause the part to be released from the fixture as shown in block 136. The machine operator can then remove the improperly welded part from the fixture as shown in block 138. The machine operator or robot must then deposit the improperly welded part into the failed part containment box, block 140, and the delivery of the failed part is confirmed automatically by the input sensor located within the failed part containment box as evidenced by the delivery confirmed test shown schematically in block 142. In the event the locked failed part containment box is utilized, the box is again automatically locked, as shown in block 144. The test computer then reenables the production line allowing the indexing of a new part into the resistance welding station in block 122.

Again, it should be noted that the preceding example was a specific embodiment of the invention adapted for use with a production line having a resistance weld station. The method and control system will be appropriately adapted for other types of parts and other inspection techniques.

Figure 6:
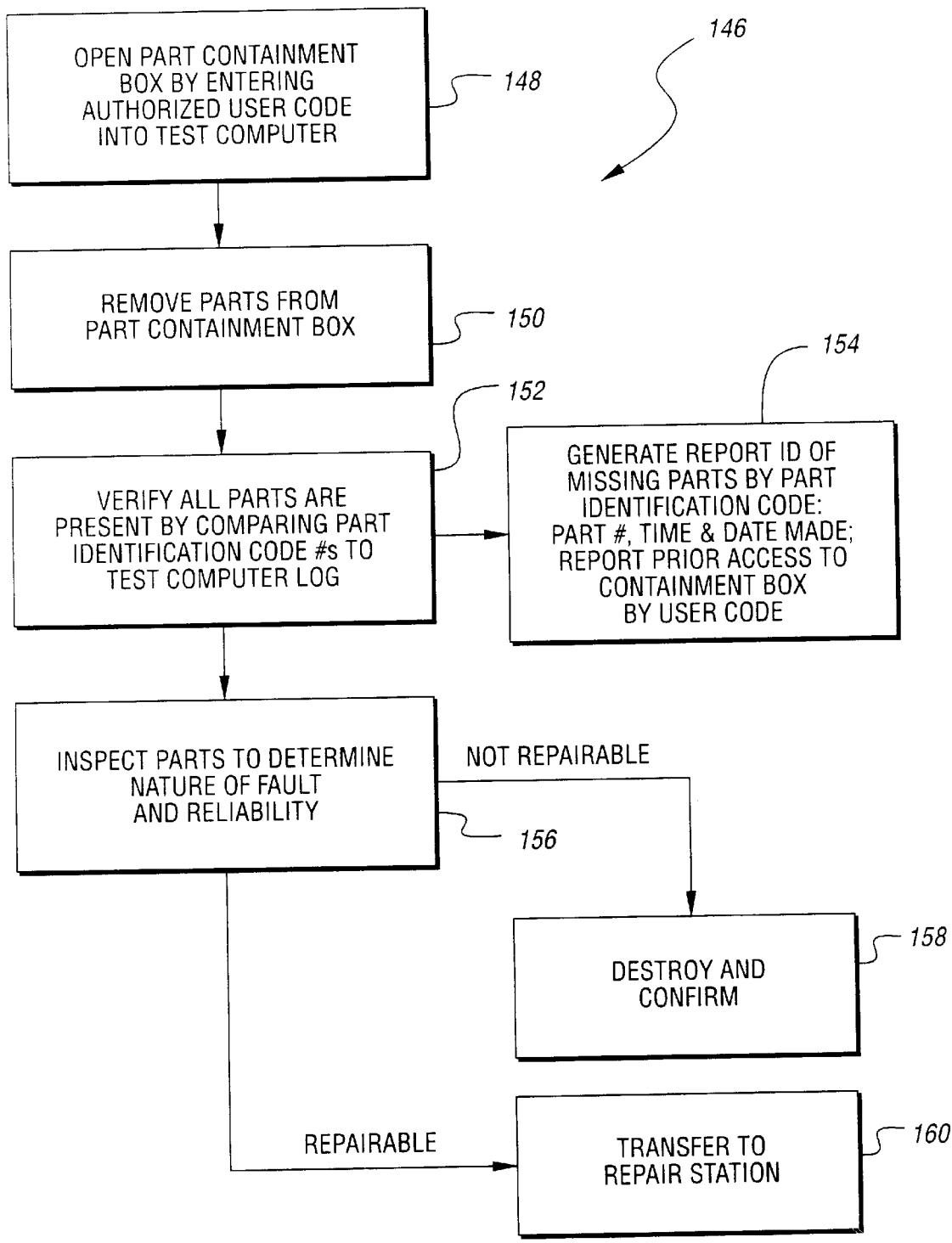
FIG. 6 is a flow chart illustrating a method of inspecting and destroying or repairing parts placed in a part containment box.

At periodic intervals, parts deposited within the failed part containment box will be removed and inspected. FIG. 6 illustrates a method of inspection 146 of failed parts which have been deposited in the failed part containment box. The initial block 148 illustrates the step of opening the failed part containment box by entering an authorized user code into the test computer. Once the box is opened, the operator removes parts from the failed part containment box at step 150 to account for all of the failed parts produced subsequent to the last box inspection as represented by block 152. The test computer is capable of generating a list of defective parts deposited in the failed part containment box in a test computer log report. In the event that defective parts are missing, the system will generate a report of missing parts and identify missing parts by part number, time and date made and report any prior access, authorized or not, to the containment box and provide access user codes, as illustrated in box 154. The parts present in the part containment box are then inspected to determine the nature of the fault and part repairability in step 156. Parts determined not to be repairable are destroyed in step 158 and repairable parts are transferred to a repair station 160. The nature of the repair will be accordingly dictated by the type of part and the nature of the fault.

While the best mode for carrying out the invention has been described in detail, those familiar with the art to which this invention relates will recognize various alternative designs and embodiments for practicing the invention as defined by the following claims.

What is claimed is:

1. A method for inspecting at least one of a plurality of parts using an inspection station having an associated storage device, the method comprising:

testing a part in the inspection station to determine if the part matches a predetermined profile;

providing a fault signal which disables the inspection station upon the determination that a part matches the predetermined profile;

removing the profile matching part from the inspection station;

storing the profile matching part in the storage device; and providing a confirmation signal which enables the inspection station when the profile matching part is removed from the inspection station and stored in the storage device.

2. The method of claim 1 further comprising:

marking the profile matching part with an identification code.

3. The method of claim 2 further comprising:

storing the identification code to verify that the profile matching part has been stored in the storage device.

4. The method of claim 1 further comprising:

generating a notification signal for an operator to remove the profile matching part from the inspection station and store said part in the storage device.

5. The method of claim 1 further comprising:

generating an alarm if the inspection station is disabled more than a predetermined time period.

6. The method of claim 1 further comprising:

unlocking the storage device in response to the fault signal to allow the profile matching part to be stored in the storage device; and locking the storage device in response to the confirmation signal to prevent access to the storage device.

7. The method of claim 1 wherein:

the predetermined profile is indicative of a defective part.

8. A method for sequentially inspecting parts using a production line having an inspection station and an associated storage device, wherein the production line is adapted to index at least one of a plurality of parts into and then out of the inspection station, the method comprising:

generating a test signal responsive to a measured parameter of a part in the inspection station;

comparing the test signal to a reference signal to determine if the part matches a predetermined profile;

providing a fault signal which disables the indexing of the production line upon the determination that a part matches the predetermined profile;

removing the profile matching part from the inspection station;

storing the profile matching part in the storage device; and providing a confirmation signal which enables the indexing of the production line when the profile matching part is removed from the inspection station and stored in the storage device.

9. The method of claim 8 further comprising:

marking the profile matching part with an identification code.

10. The method of claim 9 further comprising:

storing the identification code to verify that the profile matching part has been stored in the storage device.

11. The method of claim 8 further comprising:

generating a notification signal for an operator to remove the profile matching part from the inspection station and store said part in the storage device.

12. The method of claim 8 further comprising:

unlocking the storage device in response to the fault signal to allow the profile matching part to be stored in the storage device; and locking the storage device in response to the confirmation signal to prevent access to the storage device.

13. The method of claim 8 wherein:

the predetermined profile is indicative of a defective part.

14. A system for inspecting parts using an inspection station adapted to generate a data signal responsive to a monitored part characteristic, the system comprising:

a storage device for storing parts, the storage device being operable to generate a confirmation signal when a part is stored therein; and a comparator coupled to the inspection station and the storage device, the comparator being operable to compare the data signal to a reference signal to determine if a part in the inspection station matches a predetermined profile, the comparator being further operable to provide a fault signal for disabling the inspection station upon determining that a part matches the predetermined profile until receipt of the confirmation signal from the storage device indicating that the profile matching part has been removed from the inspection station and stored in the storage device whereupon the comparator enables the inspection station.

15. The system of claim 14 further comprising:

a programmable logic controller (PLC) coupled to the inspection station and cooperating with the comparator to disable said station.

16. The system of claim 14 wherein:

the comparator is a computer.

17. The system of claim 16 further comprising:

a marker cooperating with the computer to mark the profile matching part with an identification code.

18. The system of claim 17 wherein:

the computer stores the identification code to verify that the profile matching part has been stored in the storage device.

19. The system of claim 16 wherein:

the computer provides a notification signal to an operator to remove the part from the inspection station and store said part in the storage device upon determining that said part matches the predetermined profile.

20. The system of claim 16 wherein:

the storage device comprises a door being movable between a closed position for denying entry into the storage device and an opened position for allowing storage of parts in the storage device.

21. The system of claim 20 wherein:

the storage device further comprises a first lock assembly responsive to the computer for unlocking the door upon receiving the fault signal and for locking the door in the closed position after the computer has received the confirmation signal from the storage device.

22. The system of claim 21 wherein:

the storage device further comprises a part removal door for allowing the removal of parts therefrom, the part removal door having a second lock assembly responsive to the computer for locking and unlocking the part removal door, wherein the second lock assembly unlocks the part removal door in response to an authorized user code entered into the computer.

23. The system of claim 14 wherein:

the comparator compares the data signal to a reference signal to determine if a part is defective.

24. The system of claim 23 further comprising:

a compactor associated with the storage device for destroying defective parts.

25. A system for sequentially inspecting parts using a production line having an inspection station, wherein the production line is adapted when driven by a production line drive to index at least one of a plurality of parts into and then out of the inspection station, the system comprising:

a storage device for storing parts, the storage device being operable to generate a confirmation signal when a part is stored therein;

a test sensor for generating a test sensor signal responsive to a measured parameter of a part in the inspection station; and a comparator coupled to the production line drive, the storage device, and the test sensor, the comparator being operable to compare the test sensor signal to a reference signal to determine if a part in the inspection station matches a predetermined profile, the comparator being further operable to provide a fault signal to the production line drive for disabling the indexing of the production line upon determining that a part matches the predetermined profile until receipt of the confirmation signal from the storage device indicating that the profile matching part has been removed from the inspection station and placed in the storage device whereupon the comparator enables the indexing of the production line.

* * * * *